United States Patent [19]

Shin

[11] Patent Number: 4,937,069
[45] Date of Patent: Jun. 26, 1990

[54] ANHYDROUS SEMI-SOLID ANTIPERSPIRANT SUSPENSION

[75] Inventor: Chung T. Shin, Livingston, N.J.

[73] Assignee: Bristol-Myers Squibb Company, New York, N.Y.

[21] Appl. No.: 273,133

[22] Filed: Nov. 14, 1988

Related U.S. Application Data

[63] Continuation of Ser. No. 798,771, Nov. 15, 1985, abandoned.

[51] Int. Cl.$^5$ .......................... A61K 7/32; A61K 7/34; A61K 7/38
[52] U.S. Cl. ......................................... 424/66; 424/68
[58] Field of Search .................................... 424/68, 66

[56] References Cited

U.S. PATENT DOCUMENTS

| | | | |
|---|---|---|---|
| 4,049,792 | 9/1977 | Elsnau | 424/66 |
| 4,083,956 | 4/1978 | Shelton | 424/66 |
| 4,126,679 | 11/1978 | Davy et al. | 424/66 |
| 4,137,306 | 1/1979 | Rubino et al. | 424/DIG. 5 |
| 4,151,272 | 4/1979 | Geary et al. | 424/68 |
| 4,264,586 | 4/1981 | Collingham et al. | 424/68 |
| 4,265,878 | 5/1981 | Keil | 424/68 |
| 4,414,200 | 11/1983 | Murphy et al. | 424/63 |

FOREIGN PATENT DOCUMENTS

2139496  11/1984  United Kingdom ................. 424/66

OTHER PUBLICATIONS

Cosmetic & Toiletries, 11/1984, vol. 99, pp. 19, 20, 22, 24, 25, 36, 38, 40, 42, 44, 47, 48 and 50, Fox.
Cosmetics & Toiletries, 11/1984, vol. 99, pp. 55, 56, 58, 60, 62, 64, 65 and 66, Geria (I).
Cosmetic Technology, 3/1980, vol. 2, pp. 35-40, Hardy et al.

*Primary Examiner*—Dale R. Ore
*Attorney, Agent, or Firm*—Charles J. Zeller

[57] ABSTRACT

A substantially anhydrous semi-solid antiperspirant composition comprising (1) antiperspirant powder (2) thickening/suspending agent containing fumed silica (3) thickening/solid emollient (4) nonvolatile liquid emollient/plasticizer and (5) volatile emollient.

8 Claims, No Drawings

ANHYDROUS SEMI-SOLID ANTIPERSPIRANT SUSPENSION

This is a continuing application of application Ser. No. 798,771, filed November 15, 1985 now abandoned.

BACKGROUND OF THE INVENTION

This invention relates to semi-solid antiperspirant compositions as, for example, cream or gel products. More particularly it concerns anhydrous antiperspirant compositions of this character.

Antiperspirant compositions of a variety of dosage forms are known in prior art. These include such forms as lotions, creams, aerosol products, hard waxy sticks, etc. One dosage form which is of particular interest and toward which the present invention is directed are the semi-solid antiperspirant sticks. However, the formulation of such sticks present a number of problems some of which are outlined below.

One of these problems is the problem of syneresis or bleeding from the thixotropic gel system in which liquid contained within the semi-solid stick separates out resulting in an unappealing product. Still a further problem is that of fabric staining. In this case after the semi-solid stick product is applied to the subject, as for example to the axilla on an individual, portions of the product are transferred to clothing leaving a stain which is resistant to laundering.

Yet another problem encountered with semi-solid sticks of interest in this invention is that they are sometimes too hard. This interfers with the ability to dispense these products from a roll-on or extruding package. The undesirable wet, cold and sticky sensations experienced when aqueous based products are applied to the skin will also be dealt with in the semi-solid antipersipant stick products with which this invention is concerned.

SUMMARY OF INVENTION

It has now been discovered that semi-solid antiperspirant stick compositions may be obtained which do not have the disadvantages described above if they are constituted as compositions comprising (1) an active antrperspirant amount of at least one active antiperspirant material (hereinafter sometimes identified by the symbol "A/P"), (2) thickening/suspending agent containing fumed silica, (3)thickening/solid emollient, (4) liquid emollient/plasticizer and (5) volatile emollient in the proportions set forth in more detail below.

PRIOR ART

U.S. Pat. No. 2,087,161; issued July 13, 1937 prepared an alcoholic waxy semi-solild containing aluminum chloride and/or zinc chloride, but the product will be irritating and organoleptically not appealing because of the cooling sensation and alcoholic sting on the skin.

U.S. Pat. No. 4,083,956 prepared an anhydrous antiperspirant cream containing fatty acid ester (isopropyl myristate), Bentones (suspending/thickness agent), propylene carbonate (gel promoting agent), antiperspirant actives, fatty alcohol, and polysiloxane (anti-syneresis agent). Although the patentee perpared an anhydrous antiperspirant cream which is relatively stable and cosmetically superior to conventional antiperspirant cream products, it has a severe oil staining problem because of the high nonvolatile emollient content (30%–60%).

A product has been marketed by The Mennen Company under the trade designation "REAL SUPER DRY SOFT CONCENTRATE ANTIPERSPIRANT". "REAL" contains aluminum zirconium (Al/Zr) Tetrachlorohydrex Gly, cyclomethicone, stearyl alcohol, talc, PPG-14 butyl ether, hydrogenated castor oil, glyceryl stearate, PEG-100 stearate, and fragrance. This product, however, does not contain a thickening/suspending agent (e.g. Cab-O-Sil) as is characteristic of the products of the present invention. Moreover, the former product is not stable at elevated temperatures (e.g. at 115° F.) and experiences very substantial liquid-solid separation at these temperatures. Furthermore, it does not have the creamy characteristics of the products of this invention.

DESCRIPTION OF INVENTION

As indicated above the products of this invention are substantially anhydrous A/P semi-solids that are resistant to syneresis and oil staining. To obtain optimum results it is important that the various ingredients be included in the composition within certain defined approximate ranges. These are set forth in Table I below:

TABLE I

| INGREDIENT | CONCENTRATION RANGE % (W/W) | |
| --- | --- | --- |
| 1. A/P Active Powder | 10 | 50 |
| 2. Thickening Suspending Agents Containing Fumed Silica | 2 | 6 |
| 3. Thickening Solid Emollients | 2 | 6 |
| 4. Nonvolatile Liquid Emollient Plasticizers | 2 | 15 |
| 5. Volatile Emollient | 30 | 70 |
| 6. Other Additives | 0 | 15 |

Other additives are lubricants, fillers, stabilizing agents, antioxidants, pigments, coloring agents, perfumes, preservatives, antibacterial agents, suspending agents, gelling agents, etc. Each of these ingredients will be discussed in detail below.

The term "thickening/suspending agent" means that the ingredient selected has both designated functions i.e., it functions both as a thickening agent and as a suspending agent. Similarly, the expressions "thichening/solid emollient" and "liquid emollient/plasticizers" designate that the agent has both functions set forth in each expression.

ANTIPERSPIRANT MATERIAL

The principal active ingredient in the antiperspirant stick compositions of this invention is, of course, the antiperspirant material in the powdered state. This will ordinarily take the form of astrigent aluminum or zirconium compounds or complexes or mixtures thereof; that is, mixtures of aluminum compounds or mixtures of zirconium compounds or mixtures of aluminum compounds with zirconium compounds. Typical antiperspirant actives include impalpable aluminum chlorhydroxide and aluminum hydroxy-bromide, aluminum chloride as well as the aluminum/zirconium/glycine antiperspirant complexes disclosed in U.S. Pat. No. 3,792,068 issued Feburary 12, 1974 to Luedders et al.

The preferred aluminum compound for preparation of the Luedders et al complex is aluminum chlorhydroxide of the formula $Al_2(OH)_5Cl2H_2O$. The preferred zirconium compound for preparation of the Luedders et al complex is zirconyl hydroxychloride having the formula ZrO(OH)Cl3H2O, while the preferreed amino acid is gylcine of the formula CH2(NH2)COOH. Salts of such amino acids can also be employed in such antiperspirant complexes.

Other suitable actives for use in the present invention comprise aluminum zirconium polychlorohydrate complexes. These may be described by the general formula:

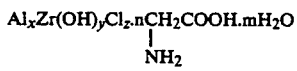

$$Al_xZr(OH)_yCl_z.nCH_2COOH.mH_2O \quad (I)$$
$$| $$
$$NH_2$$

wherein:
(a) x is a number from 2 to 10;
(b) z is a number from 3 to 8;
(c) y equals $(3x+4)-z$;
(d) the sum of $y+z$ is a number from 10 to 34;
(e) m is a number from 0 to 12;
(f) n is a number from 0 to 3 y ordinarily will have a value of from about 5 to about 29.

As will be clear from Formula I, the glycine may be bound in the complex or it may be absent. The presence or absence of the glycine in the complex will determine the amount of unbound glycine or other buffer that may be incorporated in the composition to increase the pH to a level of from about 2.5 to about 4.5 or the preferred pH of about 2.8 to about 3.8. A number of aluminum zirconium polycholorohydrate complexes are known in the prior art which are useful for the present invention. By way of example, the following may be mentioned along with their empirical formulas: aluminum zirconium tetrachlorohydrate ($Al_4Zr(OH)_{12}Cl_4$); aluminum zirconium tetracholorohydrate glycine (Wickenol #E-369) ($Al_4Zr(OH)_{12}Cl_4$).$NH_2CH_2COOH$); aluminum zirconium trichlorohydrate ($Al_4Zr(OH)_{13}Cl_3$); aluminum zirconium trichlorohydrate glycine ($Al_{10}Zr(OH)_{29}Cl_5$); aluminum zirconium pentachlorohydrate glycine ($Al_{10}Zr(OH)_{29}Cl_5$).$NH_2CH_2COOH$); aluminum zirconium octachlorohydrate ($Al_6Zr(OH)_{14}Cl_8$); aluminum zirconium octachlorohydrate glycine ($Al_6Zr(OH)_{14}Cl_8$).$NH_2CH_2COOH$). The aluminum zirconium polycholorohydrate complex can be mixed individually with the ACH and $AlCl_3.6H_2O$ in solution or powder form or in various combinations thereof. The OTC Panel on antiperspirants of the Food and Drug Administration has adopted certain nomenclatures and specifications for various aluminum zirconium polycholorohydrates that are useful in the present invention. These are set out in Table A below:

TABLE A

| Panel Adopted Nomenclature | Metal-Halide Ratio Range | Al/Zr Ratio Range |
|---|---|---|
| Aluminum zirconium trichlorohydrate | 2.1 down to but not including 1.5:1 | 2.0 up to but not including 6.0:1 |
| Aluminum zirconium tetrachlorohydrate | 1.5 down to and including 0.9:1 | 2.0 up to but not including 6.0:1 |
| Aluminum zirconium pentachlorohydrate | 2.1 down to but not including 1.5:1 | 6.0 up to and including 10.0:1 |
| Aluminum zirconium octachlorohydrate | 1.5 down to and including 0.9:1 | 6.0 up to and including 10.0:1 |

Other suitable actives for use in the present invention comprise mixtures of aluminum chloride with other aluminum salts less acidic than aluminum chloride e.g. aluminum hydroxychloride (or aluminum chlorhydroxide). These are described in Canadian Patent No. 958,388 issued Nov. 26, 1974.

The active antiperspirant material is generally present in powdered form which is suspended in the semi-solid. The quantity of the A/P actives may also vary somewhat. Usually it will be used in the range of 10% and 50% with the preferred range being between about 15% and about 26%.

THICKENING/SUSPENDING AGENT

An essential feature of the thickening/suspending agent utilized in this invention is that it contains a minimum of about 2% by weight, based on the total weight of the semi-solid composition of a fumed silica. The fumed silicas have unusually high gelling capacity for volatile and nonvolatile emollient, and are essential for the formation of the thixotropic anhydrous A/P semi-solids of the present development.

The fumed silica may comprise all of the thickening/suspending agent employed herein or may be used in conjunction with other thickening/suspending agents. Examples of other thickening/suspending agents that may be used in conjunction with the fumed silicas are precipitated silicas, hydrophobic silicas, hydrophobic bentonites and hectorites, etc. These are effective gelling agents for volatile emollients and may sometimes be used to advantage in combination with the fumed silicas.

A number of fumed silica products are availble commercially. These include such materials as Cab-O-Sil (Cabot) and Aerosil 200 (Degussa). Silica is the inorganic oxide that conforms to the formula, $SiO_2$. Other names are listed in CTFA Cosmetic Ingredient Dictionary, Second Edition, 1977, Page 291.

Precipitated silicas are available commercially as Syloid silicas (W. R. Grace & Co., Davison Chemical Div.) and Silcrons (Glidden Pigments). Silicron fine particle silica is a synthetic silica made through the hydrogel process. Sodium Silicate is converted to a gel, washed, dried and ground into a fine amorphous powder. As indicated above these may be used to advantage in conjunction with the fumed silicas in accordance with this invention.

The hydrophobic silica having a strongly hydrophobic surface. These hydrophobic products are prepared by reacting the conventional pyrogenic silica with an organosilane such as haloalkyl silanes (e.g. dimethyl dichlorosilane) under conditions which cause a chemical reaction to occur with a substantial portion of the hydroxyl groups on the surface of the pyrogenic silica. This gives a new surface structure on the outer or exposed portions of the silica which is largely composed of hydrocarbon groups. These likewise are usefully employed with the fumed silicas as indicated above.

Bentone (N L Industry) is a trade name of hydrophobic bentonites and hectorites. Bentone is prepared by reacting bentonite in a cation exchange system with an amine. Different amines are reacted to obtain a variety of Bentones. Specific examples of Bentones within the scope of the present invention are Bentone 38, Bentone 34, Bentone 27. They are available commercially from N L Industries, Inc. These too, as previously noted may be employed in conjunction with the fumed silicas for the purposes of the present development.

The quantity of thickening/suspending agents that may be incorporated in the present compositions may vary somewhat. Usually, however, it contains from about 2% to about 6%, preferably from about 3% to 5% by weight of an inorganic thickness/suspending agent.

By utilizing silicas of the particular type described and in the concentrations specified, semi-solid compositions can be formulated which exhibit minimal syneresis and which are aesthetically and cosmetically desirable for use as antiperspirant products.

THICKENING/SOLID EMOLLIENT

Another essential component of the present invention is the thickening/solid emollients. These solid emollients can be any organic waxy material which is "solid" at room temperature. Thus, any non-toxic, non-irritating organic wax having a melting point greater than about 20° C. to 120° C. can be employed in the present composition. These emollients not only absorb volatile and nonvolatile liquid emollients, but they also enhance the ease of auxillary applicability and are especially useful for improving slip.

Among various solid emollients evaluated, the following were found to be excellent gelling agents with 5%–10% cyclomethicone; stearyl alcohol, Rosswax Ozokerite, glycol stearate, Syncrowax AW1-C, Rosswax 1857, Petrolite waxes, and high melting hydrocarbon wax (FT 300 wax).

The quantity of solid emollients that may be incorporated in the present compositions may vary somewhat. Usually, however, it will fall in the range of 2% to 6%.

NONVOLATILE LIQUID EMOLLIENT/PLASTICIZERS

Another essential component of the system of the present invention is the nonvolatile liquid emollients/plasticizers. When the A/P semi-solid is prepared without liquid emollients, the product produces a waxy grainy powder on the skin after the volatile emollients evaporate. However, the addition of nonvolatile liquid emollients left a fine, creamy, silky residue on the skin. It also imparted good adherence to the skin.

The nonvolatile liquid emollients used in the present invention are, for example, straight chaim fatty acid esters (isopropyl myristate, isopropyl palmitate); branched chain fatty acid esters (2-ethyl hexyl palmitate, 2-ethyl hexyl pelarogonate); polyoxyalkylene glycol esters (polypropylene glycol 2000 monooleate); propylene glycol diesters of short chain fatty acids ($C_8$–$C_{10}$) (Neobee M-20); polyoxyethylene fatty acids; polyoxypropylene fatty ethers (Procetyl); propoxylated lower alcohol ether (Fluid AP); higher fatty alcohols (oleyl, hexadecyyl, lauryl, etc.); silicone oils (dimethyl polysiloxanes (100–2000 centistokes); low hydrocarbon fractions (Shell Sol 71), etc.

The quantity of nonvolatile liquid emollient in the present composition may vary somewhat. When large amounts of liquid emollient is used in the composition, more stable thixotropic fumed silica gel systems are produced. However, above 10% nonvolatile oil usually shows oil staining. The quantity of nonvolatile liquid emollient/plasticizers that may be incorporated in the present compositions may vary somewhat. Usually, however, it will comprise between 2% to 15% based on the total weight of the composition, the preferred range being between 3% and 10% on the same weight basis.

VOLATILE EMOLLIENTS

The Cyclomethicones are the volatile emollients of choice for use in the present invention. Because of their volatability they do not impart any oil staining.

Cyclomethicones are volatile emollients and, therefore, they do not impart any oil staining. They impart a smooth and silky feel. It was found that cyclomethicones forms unusually stable gels with fumed silica and certain solid emollients.

Typical of the volatile silicones that may be employed herein is a material that is generally referred to as cyclomethicone which is a cyclic dimethylpolysiloxane that conforms to the formula:

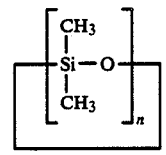

wherein n averages between 3 and 6.

The quantity of cyclomethicone contained in the semi-solid of this invention may vary. For the most part, it will fall between 30–70% of the formulation. In the preferred forms of this invention, however, the cyclomethicone will comprise between 40–60%. A number of cyclomethicone products are available commercially. These include volatile silicon 7158 from Union Carbide and a host of others (See example CTFA Cosmetic Ingredient Dictionary, Second Edition, 1977, page 71 under the entry "Cyclomethicone"). Regular polysiloxanes, viscosity range under 50 cps, also can be used in this invention as a volatile emollient.

OPTIONAL AUXILLIARY AGENTS

The antiperspirant semi-solid compositions of this invention may also contain other ingredients commonly employed in antiperspirant sticks or other forms of antiperspirant compositions. Thus, suspending agents, other gelling agents, fillers, stabilizing agents, antioxidants, pigments, coloring agents, perfumes, preservatives, antibacterial agents, lubricants, etc. may also constitute part of the semi-solid stick. Certain hydrophilic surfactants and emollients such as PPG 5 Ceteth 20, PPG 8 Ceteth 2 and PPG-9-Steareth-3 also can be added to reduce staining and to aid in forming a creamy, soft gel.

COMPOSITION PREPARATION

The antiperspirant semi-solid compositions of this invention may be made by a variety of ways known to those skilled in the art. The volatile and nonvolatile emollients, solid emollients are heated to 170° F.–175° F. until a homogeneous mixture is formed while mixing slowly. The suspending/thickening agents are added slowly while maintaining the temperature at 170° F.–175° F. Add other additives such as talc and mix until homogeneous. Add the antiperspirant actives to the batch. Mix until a homogeneous paste is formed. Mix for 15 minutes and cool to room temperature. If necessary, homogenize the batch. A homogenized batch usually demonstrates better stability.

Various types of mixing or agitation means can be employed for preparation of the present compositions. For example, the emollients, suspending/thickening agents and other additives can be admixed in a colloid mill or Osterizer to form the thixotropic gel. Suspension of the antiperspirant active within the thixotropic semi-solid gel can be accomplished with a Hobart mixer, colloid mill or Trihomomixer. The physical nature of the thixotropic semi-solid gels produced can be varied by altering the composition; agitation time and the type of shear. A skilled scientist will be able to select the composition, preparation methods suitable for providing antiperspirant semi-solid gels of desired consistency and texture.

It should be noted that the compositions of the present invention are substantially anhydrous. For purposes of the invention, substantially anhydrous compositions are those containing less than 2% by weight free moisture. Care should be taken in preparing the instant compositions to avoid use of any materials or procedures which might introduce moisture into the composition in excess of the substantially anhydrous level.

The anhydrous antiperspirant compositions of the present invention are used in the same manner as any conventional antiperspirant composition to inhibit axillary perspiration. The present compositions can be easily rubbed into the skin leaving a fine residue on the skin after the volatile emollient evaporates. The fine particles have a large surface area that when sweat is in contact with it, it starts to act instantly and continuously. Such compositions are nontacky and unusually smooth and silky. They dry quickly and give long lasting activity.

The instant compositions can be easily applied by any suitable means including the use of fingers, pads, rollons, etc. Such Compositions can be packaged in any suitable container including jars, packets, tubes, bottles, extruding devices, etc.

As indicated above the products of the present invention are semi-solid in character. Their viscosity may vary somewhat. Generally this will be in the range of from 0.1 MM cps. to about 8.8 MM cps. However, the optimum viscosity will be in the range of from about 0.3 MM cps. to about 4.4 MM cps., where MM=million. The above viscosity was calculated from Brookfield viscometer (RVT Model) using TE or TF Spindle.

The anhydrous antiperspirant semi-solid compositions of the presnet invention are illustrated by the following examples:

EXAMPLE 1

FORMULA #2141

| Components | % (W/W) |
|---|---|
| Stearyl Alcohol | 2.00 |
| Hydrogenated Castor Oil MP-80 | 3.00 |
| PPG-14 Butyl Ether | 3.00 |
| Cyclomethicone 7158 | 54.00 |
| Talc | 7.00 |
| Aluminum Zirconium Trichlorohydrex-Gly Powder | 26.00 |
| Colloidal Silicone Dioxide, M-5 | 5.00 |
| | 100.00 |

Viscosity: Spindle T-F reading (Brookfield Viscometer, Model RVT) 5 rpm, 30 sec. Overnight, 70-90

1. Add the following items into a suitable Stainless Steel steam-jacketed kettle: cyclomethicone 7158, PPG-14 butyl ether, stearyl alcohol, hydrogenated castor oil MP-80. Melt while slowly mixiing by heating to 170°-175° F. until homogeneous.
2. Add the Colloidal Silicon Dioxide, M-5 to Step 1 slowly while maintaining the temperature at 170°-175° F.
3. Add the Talc 5251 to the batch and mix until homogenous.
4. Add the aluminum zirconium trichlorohydrex-gly powder to the batch. Mix until a homogeneous paste is formed. Mix for 15 minutes and cool to room temperature.

The composition that was prepared as described above is an effective anhydrous antiperspirant composition in the form of a stable semi-solid. It exhibits minimal syneresis and does not provide an undesirable wet, sticky or cold sensation when applied and rubbed into the skin. The composition can be packaged in a cream stick dispenser (Calumet swivel cream stick) and can be dispensed through extrusion.

This composition was tested for antiperspirant activity. The general procedure employed was as described in Federal Register, Vol. 43, Number 196, October 10, 1978. It is called the gravimetric axillary antiperspirant test. Paired comparison (treated vs. treated) studies of antiperspirant effectiveness of antiperspirant semi-solid were used.

It was found that this composition is effective and similar to commercial antiperspirant solids containing Aluminum Zirconium Trichlorohydrex-Gly.

This composition was also tested for staining potential using a standard staining study protocol developed in the laboratories. The results of this test is summarized in Table I below:

TABLE I

| IDENTIFICATION | T-Shirts After 10 Applications |
|---|---|
| Formula No. 2141 | 0 = No Stain |

Staining Test Procedure:

"Hanes" 100% cotton white T-shirts were cut into 6"×8" swatches. Test materials were applied evenly onto each of two 1"×6" strips across the fabric. One gram of liquid product was pipetted and 0.5 gram of solid stick product was spread onto each strip.

Swatches were placed at 100° F. and 80-85% R.H. for 18-24 hours and laundered in a Sears Kenmore Heavy Duty Washer, Model #29921 set at Warm Wash/Warm Rinse (105° F. water), Wash and 2nd Rinse, Cotton White settings. The detergent manufacture's directions were followed as closely as possible, which were consistent with AATCC test method 124-1978. on the average, 85 grams (1 CUP) of Tide detergent was added to a 1.7-2.0 kg load and 19 gallons (medium setting) of water. Depending on load size, the amount of water (machine setting) and amount of detergent used was varied to insure AATCC test conditions: (4.4-4.7 g detergent/gallon of water, 42-54 g detergent/kg load). Swatches were dried in a Sears Kenmore Automatic Dryer set at automatic cylce, cotton setting. Ten test cycles were run.

Samples were evaluated visually for stains by at least 2 judges. the coding system for degree of stain in this study was as follows:

| Degree of Stain | Value | Comments |
|---|---|---|
| None | 0 | No stain observable |
| Very Slight | 0.5 | Barely Perceptible |
| Very Slight to Slight | 0.75 | Average of V. Slight to Slight |
| Slight | 1.0 | Obvious, undesirable but acceptable |
| Slight to Moderate | 1.5 | Borderline, Acceptable |
| Moderate | 2.0 | Unacceptable |
| Moderate to Heavy | 2.5 | Unacceptable |

-continued

| Degree of Stain | Value | Comments |
|---|---|---|
| Heavy | 3.0 | Unacceptable |

EXAMPLE 2

| BM 1957-67C | |
|---|---|
| Components | % (W/W) |
| Aluminum Zirconium Trichlorohydrex-Gly | 26.00 |
| Cab-O-Sil M-5 | 4.50 |
| Cyclomethicone 7158 | 56.50 |
| Dimethicone | 5.00 |
| PPG-9 Steareth 3 | 3.75 |
| PPG-5 Ceteth 20 | 1.25 |
| Stearyl Alcohol | 1.00 |
| Castor Wax MP 80 | 2.00 |
| | 100.00 |
| Viscosity: TE Spindle Reading (Brookfield Viscometer, Model RVT) 5 rpm, 30 sec. Overnight 59 | |

Procedure

1. Add Cab-O-Sil M-5 to a mixture of the Cyclomethicone 7158, PPG-9 Steareth 3 and PPG-5 Ceteth 20, and stir about one hour in a Hobart mixer.
2. Separately heat a mixture of the dimethicone, stearyl alcohol and castor wax MP 80 to about 175° F. until homogeneous. Add Stept 2 to Step 1 which has been heated to about 140° F. Mix about 5 minutes and cool. Add Aluminum Zirconium trichlorohydrex-Gly powder slowly and mix about 30 minutes or until homogeneous. Homogenize with a hand homogenizer. This semi-solid gel composition is stable with minimal syneresis and does not exhibit undesirable wet, sticky or cold sensation when applied and rubbed into the skin. This composition is slightly softer than Example 1. This composition was tested for staining potential using a method described in Example 1. It was found that the staining potential of this composition is zero (no staining).

EXAMPLE 3

| Components | % (W/W) |
|---|---|
| Cyclomethicone 7158 | 56.40 |
| Dimethicone (100 cs) | 2.00 |
| PPG-9 Steareth 3 | 3.75 |
| PPG-5 Ceteth 20 | 1.25 |
| Cab-O-Sil M-5 | 5.20 |
| Glycol Stearate 3789-48 | 1.60 |
| Castor Wax MP 80 | 3.80 |
| Aluminum Zirconium Trichlorohydrex-Gly | 26.00 |
| | 100.00 |
| Overnight viscosity 62 (TE Spindle, 5 rpm, 30 sec.) | |

The above composition can be prepared using a procedure similar to that described in Example 1.

This semi-solid gel composition is stable with minimal syneresis and does not exhibit undesirable wet, sticky or cold sensation when applied on the skin.

EXAMPLE 4

| BQ 1926-65 | |
|---|---|
| Components | % (W/W) |
| Cyclomethicone 7158 | 32.00 |
| *10% Bentone 38 Gel | 25.00 |
| Stearyl Alcohol | 2.00 |
| Castor Wax MP 80 | 3.00 |
| Fluid AP | 3.00 |
| Cab-O-Sil M-5 | 2.00 |
| Aluminum Zirconium Trichlorohydrex-Gly | 26.00 |
| Talc | 7.00 |
| | 100.00 |

| 0% Bentone 38 Gel | % (w/w) | |
|---|---|---|
| Bentone 38 Powder | 10.00 | The mixture |
| Alcohol SD-40, Anhydrous | 7.00 | was blended |
| Cyclomethicone 7158 | 83.00 | for 6 minutes. |
| | 100.00 | |
| Viscosity: TF Spindle Reading overnight 72 (Brookfield Viscometer, RVT Model 5 rpm, 30 sec.) | | |

The above composition can be prepared using a procedure similar to that described in Example 1.

This semi-solid gel formula exhibits minimal syneresis and does not provide undesirable wet, sticky or cold sensation when it is applied on the skin. It was also found that when the concentration of Cab-O-Sil M-5 was less than 2% in the present composition, syneresis was observed in a sample stored at elevated temperature conditions (104° F., 115° F.).

EXAMPLE 5

| BQ 2024-8 | |
|---|---|
| Components | % (W/W) |
| Cyclomethicone 7158 | 54.00 |
| $C_{15}$-$C_{18}$ Vicinal Glycol | 5.00 |
| Fluid AP | 3.00 |
| Cab-O-Sil M-5 | 5.00 |
| Talc | 7.00 |
| Aluminum Zirconium Tricholorohydrex-Gly | 26.00 |
| | 100.00 |
| Viscosity: TE Spindle reading Overnight 45-50 (Brookfield Viscometer, RVT Model 5 rpm, 30 sec. with Helipath) | |

This semi-solid gel is stable and non-tacky. It also provides no undesirable wet and cold sensation when applied on the skin.

EXAMPLE 6

| BQ 2024-9 | |
|---|---|
| Components | % (W/W) |
| Cyclomethicone 7158 | 54.00 |
| Castor Wax MP 80 | 5.00 |
| Fluid AP | 3.00 |
| Cab-O-Sil M-5 | 5.00 |
| Talc | 7.00 |
| Aluminum Zirconium Trichlorohydrex-Gly | 26.00 |
| | 100.00 |
| Viscosity: TF Spindle reading Overnight 50-55 (Brookfield Viscometer, RVT Model 5 rpm, 30 sec.) | |

EXAMPLE 7

| BQ 2024-11 | |
|---|---|
| Components | % (W/W) |
| Cyclomethicone 7158 | 54.00 |

-continued

BQ 2024-11

| Components | % (W/W) |
|---|---|
| Castor Wax MP 80 | 2.50 |
| Gylcol Stearate | 2.50 |
| Cab-O-Sil M-5 | 5.00 |
| Aluminum Zirconium Trichlorohydrex-Gly | 26.00 |
| Fluid AP | 3.00 |
| Talc | 7.00 |
| | 100.00 |

Viscosity: TE Spindle reading Overnight 65–70 (Brookfield Viscometer, RVT Model 5 rpm, 30 sec.)

EXAMPLE 8

BQ 2024-27

| Components | % (W/W) |
|---|---|
| Cyclomethicone 7158 | 54.50 |
| Castor Wax MP 80 | 2.50 |
| Rosswax Ozokerite | 2.50 |
| Cab-O-Sil M-5 | 4.50 |
| Aluminum Zirconium Trichlorohydrex-Gly | 26.00 |
| Fluid AP | 3.00 |
| Talc | 7.00 |
| | 100.00 |

Viscosity: TE Spindle Reading 45–55 (Brookfield Viscometer, RVT Model with Helipath, 5 rpm, 30 sec.)

EXAMPLE 9

BQ 2024-29

| Components | % (W/W) |
|---|---|
| Cyclomethicone 7158 | 54.50 |
| Glycol Stearate | 2.50 |
| Petrolite Beesquare 195 White Wax | 2.50 |
| Cab-O-Sil M-5 | 4.50 |
| Aluminum Zirconium Trichlorohydrex-Gly | 26.00 |
| Fluid AP | 3.00 |
| Talc | 7.00 |
| | 100.00 |

Viscosity: TE Spindle Reading 60–65 (Brookfield Viscometer, RVT Model with Helipath, 5 rpm, 30 sec.)

Although the invention has been described with reference to specific forms thereof, it will be understood that many changes and modifications may be made without departing from the spirit of this invention.

What is claimed is:

1. A substantially anhydrous semisolid antiperspirant composition consisting essentially of, based on the total weight of the composition:
   (1) from about 10% to about 50% of active antiperspirant powder;
   (2) from about 2% to about 6% of thickening/suspending agent containing fumed silica in an amount to constitute a minimum of about 2% by weight of the total composition;
   (3) from about 2% to about 6% of thickening/solid emollient;
   (4) from about 2% to about 15% of nonvolatile liquid emollient/plasticizer, and
   (5) from about 30% to about 70% of volatile emollient, said composition, which is in the form of a cream and has a viscosity of from about 100,000 cps to about 8,800,000 cps, exhibiting minimal syneresis, the composition when applied to skin leaving a creamy residue and exhibiting not more than slight-to-moderate staining of fabric.

2. A composition according to claim 1 wherein said volatile emollient is a volatile cyclomethicone.

3. A composition according to claim 3 wherein said thickening/solid emollient is an organic wax having a melting point greater than about 20° C.

4. A composition according to claim 2 wherein said thickening/solid emollient is an organic wax having a melting point less than about 120° C.

5. A composition according to claim 2 wherein said nonvolatile liquid emollient is selected from the group consisting of straight chain fatty acid esters, branched chain fatty acid esters, polyoxyalkylene glycol ethers, propylene glycol diesters of short chain fatty acids, polyoxyethylene fatty acids, polyoxypropylene fatty ethers, propoxylated lower alcohol ethers, higher fatty alcohols, nonvolatile silicone oils, lower hydrocarbon fractions.

6. A composition according to claim 2 wherein said antiperspirant material is Aluminum Zirconium Polychlorohydrex-Gly.

7. A composition according to claim 2 wherein said thickening/suspending agent also contains a material selected from the group consisting of precipitated silicas, hydrophobic silicas, hydrophobic bentonites, hydrophobic hectorites and mixtures thereof.

8. A composition according to claim 2 having a viscosity in the range of from about 300,000 cps. to about 4,400,000 cps.

* * * * *